United States Patent
Yaver et al.

(10) Patent No.: US 7,056,718 B2
(45) Date of Patent: Jun. 6, 2006

(54) POLYPEPTIDES HAVING OXALOACETATE HYDROLASE ACTIVITY AND NUCLEIC ACIDS ENCODING SAME

(75) Inventors: Debbie Yaver, Davis, CA (US); Barbara Cherry, Davis, CA (US); Jeffrey Murrell, Winters, CA (US)

(73) Assignee: Novozymes, Inc., Davis, CA (US)

( * ) Notice: Subject to any disclaimer, the term of this patent is extended or adjusted under 35 U.S.C. 154(b) by 0 days.

(21) Appl. No.: 11/193,981

(22) Filed: Jul. 29, 2005

(65) Prior Publication Data

US 2005/0273880 A1 Dec. 8, 2005

Related U.S. Application Data

(62) Division of application No. 10/913,142, filed on Aug. 6, 2004, now Pat. No. 6,939,701.

(60) Provisional application No. 60/493,708, filed on Aug. 8, 2003.

(51) Int. Cl.
*C07H 21/04* (2006.01)
*C12N 9/24* (2006.01)
*C12N 9/42* (2006.01)

(52) U.S. Cl. .................. 435/195; 435/200; 435/320.1; 435/7.31; 435/252.3; 435/252.33; 530/500; 530/388.26; 536/23.2; 800/295

(58) Field of Classification Search ............... 435/195, 435/200, 320.1, 7.31, 252.3, 252.33, 69.1; 530/500, 388.26; 536/23.2; 800/295
See application file for complete search history.

(56) References Cited

U.S. PATENT DOCUMENTS 6,544,765 B1 * 4/2003 Hjort et al. ................ 435/195

FOREIGN PATENT DOCUMENTS

WO    WO 00/52576    9/2000

OTHER PUBLICATIONS

Munir E. et. al. A Physiological role for oxalic acid biosynthesis in the wood rotting basidiomycetes Fomitopsis palustris. 2001. Proceedings to the National Academy of Science. vol. 98, No. 20, p. 11126-11130.*
Urzua et al., 1995, *FEBS Letters* 371: 132-136.
Kubicek et al., 1988, *Appl. Environ. Microb.* 55: 633-637.
Balmforth and Thomson, 1984, *Biochem. J.* 218: 341-342.
Messner and Srebotnik 1994, *FEMS Microbiology Rev.* 13: 351-364.
Scott and Swaney, 1998, *Tappi J.* 81: 153-175.
Blanchette et al., 1988, *Biomass* 15: 93-101.
Blanchette, 1991, *Annu. Rev. Phytopathol.* 29: 381-398.
Blanchette, 1994, *Can. J. Botany* 73: S999-S1010.
Blanchette et al., 1997, *J. Biotechnology* 53: 203-213.
Breen and Singleton, 1999, *Curr. Opinion Biotech.* 10: 252-258.

* cited by examiner

*Primary Examiner*—Rebecca E. Prouty
*Assistant Examiner*—Kagnew Gebreyesus
(74) *Attorney, Agent, or Firm*—Robert L. Starnes

(57) ABSTRACT

The present invention relates to isolated polypeptides having oxaloacetate hydrolase activity and isolated polynucleotides encoding the polypeptides. The invention also relates to nucleic acid constructs, vectors, and host cells comprising the polynucleotides as well as methods for producing and using the polypeptides.

16 Claims, 2 Drawing Sheets

```
          M  P  G  L  D  Y  F  R  E  T  E  T  T  Q  V  P  A  P  V  A
   1  ATGCCGGGCCTTGACTACTTCCGCGAGACTGAGACCACTCAGGTCCCTGCCCCAGTTGCG
          T  Q  E  P  V  E  S  E  P  S  S  P  A  D  T  M  P  I  D  N
  61  ACGCAAGAGCCCGTAGAGTCTGAGCCTTCTTCCCCTGCCGACACCATGCCCATCGACAAC
          G  L  T  P  A  P  G  V  Y  Y  N  P  R  L  D  P  K  N  Y  L
 121  GGTCTTACCCCTGCTCCTGGTGTCTACTACAACCCCCGCCTCGACCCCAAAAACTACCTC
          E  G  P  L  S  W  N  P  S  T  R  L  R  Q  L  L  A  R  P  G
 181  GAAGGTCCTCTCTCGTGGAACCCCTCGACCCGTCTCCGGCAACTGCTGGCGCGTCCTGGT
          I  V
 241  ATCGTTGTAAGTTCCTTCGTACACTAGAGATGAATTGCACGCTGATTAAATTTTCGATTT
             V  A  P  G  I  C  D  G  I  S  A  R  C  A  L  E  A  G  F
 301  GCAGGTGGCGCCTGGTATCTGCGATGGCATCAGCGCACGCTGTGCCTTGGAGGCGGGCTT
          D  C  M  Y  Q  S
 361  CGACTGCATGTACCAGAGGTACGTCCAGGATCGAATTGTATGAATTTCGAAGCTGATTTG
                G  A  A  T  T  A  S  R  L  G  M  P  D  L  A  I
 421  AACGTCTTCAGCGGCGCCGCCACCACCGCATCCCGTCTCGGCATGCCTGACCTCGCAATC
          A  T  L  N  D  F  V  Q  S  A  Q  M  V  C  S  L  N  P  S  V
 481  GCAACTCTCAACGACTTCGTTCAGAGCGCACAGATGGTCTGCAGCTTGAACCCCTCGGTA
          P  V  I  A  D  A  D  T  G  F  G  G  P  A  M  V  A  R  T  V
 541  CCCGTCATTGCCGACGCAGACACCGGCTTCGGTGGTCCCGCTATGGTTGCTCGTACGGTC
          T  Q  Y  A  R  A  G  V  A  G  L  H  I  E  D  Q  V  Q  T  K
 601  ACGCAATACGCGCGCGCAGGTGTCGCCGGACTCCACATCGAGGACCAGGTTCAGACCAAG
          R  C  G  H  L  L  G  K  Q  V  V  S  R  E  E  F  I  T  R  I
 661  CGCTGCGGCCACCTGCTTGGCAAGCAGGTCGTCTCCCGCGAGGAATTCATCACTCGCATT
          R  A  A  V  I  A  R  D  S  I  P  G  G  S  D  F
 721  CGGGCAGCCGTCATCGCACGCGACTCCATCCCGGGAGGCTCGGACTTCGTAAGTCCACAT
                                                     V  I  I  G  R  T
 781  CCAAATTCAATTGTCGACGAATTTGAATTAACAGCACTCGTAGGTCATCATTGGCCGCAC
             D  S  A  Q  V  L  G  M  E  E  A  I  I  R  L  K  L  A  A  D
 841  GGACTCTGCCCAGGTCTTGGGCATGGAGGAGGCGATCATCCGCCTGAAGCTCGCCGCCGA
          A  G  A  D  V  C  F  I  E  G  V  R  T  A  E  L  L  K  S  T
 901  TGCCGGAGCGGATGTGTGCTTCATCGAAGGTGTGCGTACCGCCGAGCTCCTGAAGTCCAC
          V  A  A  L  A  P  K  P
 961  GGTGGCTGCGCTGGCGCCCAAGCCTGTGAGTTCTCCTCACCAGATCGGTATCGAAGCTGC
                                  V  L  V  N  V  I  S  G  G  L  T  P  S  F  T
1021  CTAACATTTCTATCAGGTCCTCGTCAATGTCATCTCGGGTGGTCTGACCCCCTCCTTCAC
          C  Q  E  A  E  E  M  G  A  K  I  I
1081  CTGCCAAGAGGCCGAGGAGATGGGTGCCAAGATTATCAGTAAGTCTTCTCAAAGTGAGCC
                                              I  F  S  L  E  S  C  V  A  A  V
1141  ACCTCTGTGTACTGATAGCCGGCGCAATCTTCTCTCTCGAGTCTTGCGTCGCGGCCGTGC
          H  G  I  R  A  A  M  H  S  L  K  K  T  G  T  D  F  S  S  A
1201  ACGGTATCCGCGCGGCGATGCACTCCCTGAAGAAGACCGGTACAGACTTCTCGTCTGCGA
          K  G  M  D  P  K  A  F  F  E  V  M
1261  AGGGCATGGACCCCAAGGCGTTCTTCGAGGTCATGGGTATGTCGTGCCACCAATGCCAAT
                                                     G  L  H  D  V  I  E  L
1321  TTCCTCACAGGCCTGATGGGTGATCATTTGCAACAGGTCTCCACGATGTCATCGAGCTCG
          D  A  Q  A  G  G  K  A  F  E  V  V  *
1381  ACGCCCAGGCTGGTGGCAAGGCGTTCGAAGTTGTCTAG
```

Fig. 1

POLYPEPTIDES HAVING OXALOACETATE HYDROLASE ACTIVITY AND NUCLEIC ACIDS ENCODING SAME

CROSS-REFERENCE TO RELATED APPLICATIONS

This application is a divisional of U.S. application Ser. No. 10/913,142 filed on Aug. 6, 2004 now U.S. Pat. No. 6,939,701, which claims the benefit of U.S. Provisional Application No. 60/493,708, filed Aug. 8, 2003, which applications are incorporated herein by reference.

BACKGROUND OF THE INVENTION

1. Field of the Invention

The present invention relates to isolated polypeptides having oxaloacetate hydrolase activity and isolated polynucleotides encoding the polypeptides. The invention also relates to nucleic acid constructs, vectors, and host cells comprising the polynucleotides as well as methods for producing and using the polypeptides.

2. Description of the Related Art

Lignin is an aromatic polymer occurring in the woody tissue of higher plants. Due to its hydrophobicity and complex random structure lacking regular hydrolyzable bonds, lignin is poorly degraded by most organisms. The best degraders of lignin are white rot fungi that produce extracellular peroxidases and laccases, which are involved in the initial attack of lignin.

Manganese-dependent peroxidase is a frequently encountered peroxidase produced by white rot fungi (Urzúa et al., 1995, *FEBS Letters* 371: 132–136). The enzyme catalyzes the oxidation of $Mn^{2+}$ to $Mn^{3+}$, which in turn can oxidize residues present in lignin. The peroxidase has a catalytic cycle involving a 2-electron oxidation of its heme by hydrogen peroxide to form compound I. Compound I can be reduced by Mn(II) or a phenolic substrate to compound II, the one electron form of the enzyme. The best reducing substrate for compounds I and II is Mn(II), a metal naturally present in wood. The Mn(III) formed oxidizes other substrates.

Organic acids such as oxalate, glyoxylate and lactate are known to have an important role in the mechanism of manganese-dependent peroxidase and lignin degradation. Mn(III) is stripped from the enzyme by organic acids, and the produced Mn(III)-organic acid complex acts as a diffusible mediator in the oxidation of lignin by manganese-dependent peroxidase. Mn(III) can also oxidize organic acids, yielding radicals. The organic acids may also be supplied from the degradation of lignin and by microorganisms.

Several pathways leading to oxalate have been elucidated. One involves the cleavage of oxaloacetate by oxaloacetate hydrolase to form oxalic acid and acetate (Kubicek et al., 1988, *Appl. Environ. Microb.* 55: 633–637). Another pathway involves the oxidation of glyoxylate to oxalic acid by the enzyme NAD-glyoxylate dehydrogenase (Balmforth and Thomson, 1984, *Biochem. J.* 218: 341–342).

WO 2000/50576 describes an *Aspergillus niger* oxaloacetate hydrolase gene and fungal host cells made deficient in such a gene.

There is a need in the art for improving the lignin degradative ability of strains by increasing the production of enzymes involved in degrading lignin. For example, *Ceriporiopsis subvermispora* is currently used for biopulping and an engineered strain thereof with an improved lignin degradation capability would be particularly advantageous. Pretreatment of wood chips with *Ceriporiopsis subvermispora* prior to mechanical pulping has been shown to reduce energy consumption by 30–45% (Messner and Srebotnik 1994, *FEMS Microbiology Rev.* 13: 351–364; Scott and Swaney, 1998, *TAPPI J.* 81: 153–175; Scott et al., 2000, Recent Developments in Biopulping Technology at Madison, Wis. In: L Viikari and R Lantto, ed. Progress in Biotechnology 21: Biotechnology in the Pulp and Paper Industry: 8th ICBPPI Meeting. Amsterdam: Elsevier Science B.V. pp 61–71.). While the mechanism(s) of biopulping are unknown, *Ceriporiopsis subvermispora* colonization of wood appears to involve at least two stages: an initial rapid colonization which softens wood without affecting fiber strength or lignin content, and later an efficient depolymerization and mineralization of lignin (Blanchette et al., 1988, *Biomass* 15: 93–101; Blanchette, 1991, *Annu. Rev. Phytopathol.* 29: 381–398; Blanchette, 1994, *Can. J. Botany* 73: S999–S1010; Blanchette et al., 1997, *J. Biotechnology* 53: 203–213; Breen and Singleton, 1999, *Curr. Opinion Biotech.* 10: 252–258).

It is an object of the present invention to provide improved polypeptides having oxaloacetate hydrolase activity and nucleic acids encoding the polypeptides.

SUMMARY OF THE INVENTION

The present invention relates to isolated polypeptides having oxaloacetate hydrolase activity selected from the group consisting of:

(a) a polypeptide having an amino acid sequence which has at least 70% identity with SEQ ID NO: 2;

(b) a polypeptide which is encoded by a nucleotide sequence which hybridizes under at least medium stringency conditions with (i) SEQ ID NO: 1, (ii) the cDNA sequence contained in SEQ ID NO: 1, or (iii) a complementary strand of (i) or (ii); and (c) a variant comprising a conservative substitution, deletion, and/or insertion of one or more amino acids of SEQ ID NO: 2.

The present invention also relates to isolated polynucleotides encoding polypeptides having oxaloacetate hydrolase activity, selected from the group consisting of:

(a) a polynucleotide encoding a polypeptide having an amino acid sequence which has at least 70% identity with SEQ ID NO: 2;

(b) a polynucleotide having at least 70% identity with SEQ ID NO: 1; and (c) a polynucleotide which hybridizes under at least medium stringency conditions with (i) SEQ ID NO: 1, (ii) the cDNA sequence contained in SEQ ID NO: 1, or (iii) a complementary strand of (i) or (ii).

The present invention also relates to nucleic acid constructs, recombinant expression vectors, and recombinant host cells comprising the polynucleotides.

The present invention also relates to methods for producing such polypeptides having oxaloacetate hydrolase activity comprising (a) cultivating a recombinant host cell comprising a nucleic acid construct comprising a polynucleotide encoding the polypeptide under conditions conducive for production of the polypeptide; and (b) recovering the polypeptide.

The present invention further relates to methods of delignifying a material comprising (a) treating the material with a microorganism comprising a nucleic acid construct of the invention, and (b) recovering the treated material.

BRIEF DESCRIPTION OF THE FIGURES

FIG. 1 shows the genomic DNA sequence and the deduced amino acid sequence of a *Ceriporiopsis subvermispora* FPL 104807SS-5 (Forest Products Laboratory, Madison, Wis.) oxaloacetate hydrolase (SEQ ID NOs: 1 and 2, respectively).

FIG. 2 shows a restriction map of pBM115a.

Definitions

Figure 2:
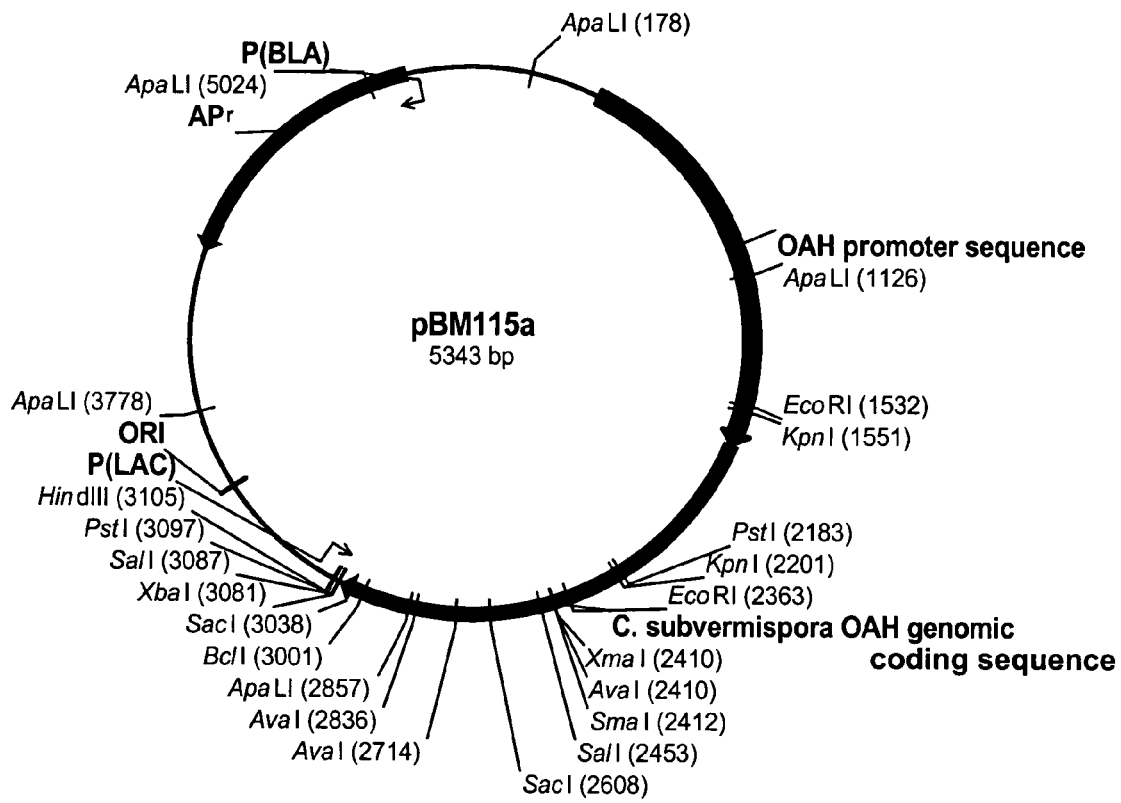

Oxaloacetate hydrolase activity: The term "oxaloacetate hydrolase activity" is defined herein as an oxaloacetate acetylhydrolase activity which catalyzes the hydrolysis of oxaloacetate to oxalic acid and acetate. Oxaloacetate hydrolases are classified as belonging to EC 3.7.1.1. For purposes of the present invention, oxaloacetate hydrolase activity is determined according to the procedure described by Lenz et al., 1976, *Eur. J. Biochem.* 65: 225–236. One unit of oxaloacetate hydrolase activity is defined as 1.0 μmole of oxalic acid produced per minute at 30° C., pH 7.5.

The polypeptides of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the oxaloacetate hydrolase activity of the polypeptide consisting of the amino acid sequence shown as SEQ ID NO: 2.

Isolated polypeptide: The term "isolated polypeptide" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE.

Substantially pure polypeptide: The term "substantially pure polypeptide" denotes herein a polypeptide preparation which contains at most 10%, preferably at most 8%, more preferably at most 6%, more preferably at most 5%, more preferably at most 4%, at most 3%, even more preferably at most 2%, most preferably at most 1%, and even most preferably at most 0.5% by weight of other polypeptide material with which it is natively associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation.

The polypeptides of the present invention are preferably in a substantially pure form. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods.

Herein, the term "substantially pure polypeptide" is synonymous with the terms "isolated polypeptide" and "polypeptide in isolated form."

Identity: The relatedness between two amino acid sequences or between two nucleotide sequences is described by the parameter "identity".

For purposes of the present invention, the degree of identity between two amino acid sequences is determined by the Clustal method (Higgins, 1989, *CABIOS* 5: 151–153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=1, gap penalty=3, windows=5, and diagonals=5.

For purposes of the present invention, the degree of identity between two nucleotide sequences is determined by the Wilbur-Lipman method (Wilbur and Lipman, 1983, *Proceedings of the National Academy of Science USA* 80: 726–730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=3, gap penalty=3, and windows=20.

Polypeptide Fragment: The term "polypeptide fragment" is defined herein as a polypeptide having one or more amino acids deleted from the amino and/or carboxyl terminus of SEQ ID NO: 2 or a homologous sequence thereof, wherein the fragment has oxaloacetate hydrolase activity. Preferably, a fragment contains at least 320 amino acid residues, more preferably at least 335 amino acid residues, and most preferably at least 350 amino acid residues.

Subsequence: The term "subsequence" is defined herein as a nucleotide sequence having one or more nucleotides deleted from the 5' and/or 3' end of SEQ ID NO: 1 or a homologous sequence thereof, wherein the subsequence encodes a polypeptide fragment having oxaloacetate hydrolase activity. Preferably, a subsequence contains at least 960 nucleotides, more preferably at least 1005 nucleotides, and most preferably at least 1050 nucleotides.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide which is at least 20% pure, preferably at least 40% pure, more preferably at least 60% pure, even more preferably at least 80% pure, most preferably at least 90% pure, and even most preferably at least 95% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form. In particular, it is preferred that the polynucleotides disclosed herein are in "essentially pure form", i.e., that the polynucleotide preparation is essentially free of other polynucleotide material with which it is natively associated. Herein, the term "substantially pure polynucleotide" is synonymous with the terms "isolated polynucleotide" and "polynucleotide in isolated form." The polynucleotides may be of genomic, cDNA, RNA, semisynthetic, synthetic origin, or any combinations thereof.

cDNA: The term "cDNA" is defined herein as a DNA molecule which can be prepared by reverse transcription from a mature, spliced, mRNA molecule obtained from a eukaryotic cell. cDNA lacks intron sequences that are usually present in the corresponding genomic DNA. The initial, primary RNA transcript is a precursor to mRNA which is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

Control sequence: The term "control sequences" is defined herein to include all components, which are necessary or advantageous for the expression of a polynucleotide encoding a polypeptide of the present invention. Each control sequence may be native or foreign to the nucleotide sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG. The coding sequence may a DNA, cDNA, or recombinant nucleotide sequence.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the invention, and which is operably linked to additional nucleotides that provide for its expression.

Host cell: The term "host cell", as used herein, includes any cell type which is susceptible to transformation, transfection, transduction, and the like with a nucleic acid construct or expression vector comprising a polynucleotide of the present invention.

Modification: The term "modification" means herein any chemical modification of the polypeptide consisting of the SEQ ID NO: 2 or a homologous sequence thereof as well as genetic manipulation of the DNA encoding that polypeptide. The modification can be substitution, deletion and/or insertion of one or more amino acids as well as replacements of one or more amino acid side chains.

Artificial variant: When used herein, the term "artificial variant" means a polypeptide having oxaloacetate hydrolase activity produced by an organism expressing a modified nucleotide sequence of SEQ ID NO: 1 or a homologous sequence thereof. The modified nucleotide sequence is obtained through human intervention by modification of the nucleotide sequence disclosed in SEQ ID NO: 1 or a homologous sequence thereof.

DETAILED DESCRIPTION OF THE INVENTION

Polypeptides Having Oxaloacetate Hydrolase Activity

In a first aspect, the present invention relates to isolated polypeptides having an amino acid sequence which has a degree of identity to SEQ ID NO: 2 of at least 70%, preferably at least 75%, more preferably at least 80%, more preferably at least 85%, even more preferably at least 90%, most preferably at least 95%, and even most preferably at least 97%, which have oxaloacetate hydrolase activity (hereinafter "homologous polypeptides"). In a preferred aspect, the homologous polypeptides have an amino acid sequence which differs by ten amino acids, preferably by five amino acids, more preferably by four amino acids, even more preferably by three amino acids, most preferably by two amino acids, and even most preferably by one amino acid from SEQ ID NO: 2.

A polypeptide of the present invention preferably comprises the amino acid sequence of SEQ ID NO: 2 or an allelic variant thereof; or a fragment thereof that has oxaloacetate hydrolase activity. In a preferred aspect, a polypeptide comprises the amino acid sequence of SEQ ID NO: 2. In another preferred aspect, a polypeptide consists of the amino acid sequence of SEQ ID NO: 2 or an allelic variant thereof; or a fragment thereof that has oxaloacetate hydrolase activity. In another preferred aspect, a polypeptide consists of the amino acid sequence of SEQ ID NO: 2.

In a second aspect, the present invention relates to isolated polypeptides having oxaloacetate hydrolase activity which are encoded by polynucleotides which hybridize under very low stringency conditions, preferably low stringency conditions, more preferably medium stringency conditions, more preferably medium-high stringency conditions, even more preferably high stringency conditions, and most preferably very high stringency conditions with (i) SEQ ID NO: 1, (ii) the cDNA sequence contained in SEQ ID NO: 1, (iii) a subsequence of (i) or (ii), or (iv) a complementary strand of (i), (ii), or (iii) (J. Sambrook, E. F. Fritsch, and T. Maniatus, 1989, *Molecular Cloning, A Laboratory Manual*, 2d edition, Cold Spring Harbor, N.Y.). A subsequence of SEQ ID NO: 1 contains at least 100 contiguous nucleotides or preferably at least 200 contiguous nucleotides. Moreover, the subsequence may encode a polypeptide fragment which has oxaloacetate hydrolase activity.

The nucleotide sequence of SEQ ID NO: 1 or a subsequence thereof, as well as the amino acid sequence of SEQ ID NO: 2 or a fragment thereof, may be used to design a nucleic acid probe to identify and clone DNA encoding polypeptides having oxaloacetate hydrolase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes which are at least 600 nucleotides, at least preferably at least 700 nucleotides, more preferably at least 800 nucleotides, or most preferably at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other organisms may, therefore, be screened for DNA which hybridizes with the probes described above and which encodes a polypeptide having oxaloacetate hydrolase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 1 or a subsequence thereof, the carrier material is used in a Southern blot.

For purposes of the present invention, hybridization indicates that the nucleotide sequence hybridizes to a labeled nucleic acid probe corresponding to the nucleotide sequence shown in SEQ ID NO: 1, the cDNA sequence contained in SEQ ID NO: 1, its complementary strand, or a subsequence thereof, under very low to very high stringency conditions. Molecules to which the nucleic acid probe hybridizes under these conditions can be detected using X-ray film.

In a preferred aspect, the nucleic acid probe is SEQ ID NO: 1 or the complementary strand thereof. In another preferred aspect, the nucleic acid probe is a polynucleotide sequence which encodes the polypeptide of SEQ ID NO: 2, or a subsequence thereof. In another preferred aspect, the nucleic acid probe is the polynucleotide sequence contained in plasmid pBM115a which is contained in *Escherichia coli* NRRL B-30669, wherein the polynucleotide sequence thereof encodes a polypeptide having oxaloacetate hydrolase activity.

For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

Under salt-containing hybridization conditions, the effective $T_m$ is what controls the degree of identity required between the probe and the filter bound DNA for successful hybridization. The effective $T_m$ may be determined using the formula below to determine the degree of identity required for two DNAs to hybridize under various stringency conditions.

$$\text{Effective } T_m = 81.5 + 16.6(\log M[\text{Na}^+]) + 0.41(\% \ G+C) - 0.72(\% \text{ formamide})$$

The G+C content of SEQ ID NO: 1 is 58.3%. For medium stringency, the formamide is 35% and the Na⁺ concentration for 5×SSPE is 0.75 M. Applying this formula to these values, the Effective $T_m$ is 78.13° C.

Another relevant relationship is that a 1% mismatch of two DNAs lowers the $T_m$ by 1.4° C. To determine the degree of identity required for two DNAs to hybridize under medium stringency conditions at 42° C., the following formula is used:

$$\% \text{ Homology} = 100 - [(\text{Effective } T_m - \text{Hybridization Temperature})/1.4]$$

Applying this formula to the values, the degree of identity required for two DNAs to hybridize under medium stringency conditions at 42° C. is 74.19%.

In a third aspect, the present invention relates to artificial variants comprising a conservative substitution, deletion, and/or insertion of one or more amino acids of SEQ ID NO: 2 or a homologous sequence thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, *Science* 244: 1081–1085). In the latter technique, single alanine mutations are introduced at every residue in the molecule, and the resultant mutant molecules are tested for biological activity (i.e., oxaloacetate hydrolase activity) to identify amino acid residues that are critical to the activity of the molecule. See also, Hilton et al., 1996, *J. Biol. Chem.* 271: 4699–4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306–312; Smith et al, 1992, *J. Mol. Biol.* 224: 899–904; Wlodaver et al., 1992, *FEBS Lett.* 309:59–64. The identities of essential amino acids can also be inferred from analysis of identities with polypeptides which are related to a polypeptide according to the invention.

Single or multiple amino acid substitutions can be made and tested using known methods of mutagenesis, recombination, and/or shuffling, followed by a relevant screening procedure, such as those disclosed by Reidhaar-Olson and Sauer, 1988, *Science* 241: 53–57; Bowie and Sauer, 1989, *Proc. Natl. Acad. Sci. USA* 86: 2152–2156; WO 95/17413; or WO 95/22625. Other methods that can be used include error-prone PCR, phage display (e.g., Lowman et al., 1991, *Biochem.* 30:10832–10837; U.S. Pat. No. 5,223,409; WO 92/06204), and region-directed mutagenesis (Derbyshire et al., 1986, *Gene* 46:145; Ner et al., 1988, *DNA* 7:127).

Mutagenesis/shuffling methods can be combined with high-throughput, automated screening methods to detect activity of cloned, mutagenized polypeptides expressed by host cells. Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of SEQ ID NO: 2 is 10, preferably 9, more preferably 8, more preferably 7, more preferably 6, more preferably 5, more preferably 4, even more preferably 3, most preferably 2, and even most preferably 1.

Sources of Polypeptides Having Oxaloacetate Hydrolase Activity

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide of the present invention may be a fungal polypeptide, and more preferably a yeast polypeptide such as a *Candida*, *Kluyveromyces*, *Pichia*, *Saccharomyces*, *Schizosaccharomyces*, or *Yarrowia* polypeptide; or more preferably a filamentous fungal polypeptide such as an *Acremonium*, *Aspergillus*, *Aureobasidium*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Piromyces*, *Schizophyllum*, *Talaromyces*, *Thermoascus*, *Thielavia*, *Tolypocladium*, or *Trichoderma* polypeptide.

In a preferred aspect, the polypeptide is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* polypeptide having oxaloacetate hydrolase activity.

In another preferred aspect, the polypeptide is an *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, *Aspergillus oryzae*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola insolens*, *Humicola lanuginosa*, *Mucor miehei*, *Myceliophthora thermophila*, *Neurospora crassa*, *Penicillium purpurogenum*, *Trichoderma harzianum*, *Trichoderma koningii*, *Trichoderma longibrachiatum*, *Trichoderma reesei*, or *Trichoderma viride* polypeptide.

In another preferred aspect, the polypeptide is a *Ceriporiopsis aneirina*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, or *Ceriporiopsis subvermispora* polypeptide.

In a more preferred aspect, the polypeptide is a *Ceriporiopsis subvermispora* polypeptide, and most preferably a *Ceriporiopsis subvermispora* FPL 104807SS-5 (Forest Products Laboratory, Madison, Wis.) polypeptide, e.g., the polypeptide of SEQ ID NO: 2.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide sequence encoding a polypeptide has been detected with the probe(s), the polynucleotide can be isolated or cloned by utilizing techniques which are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Polynucleotides

The present invention also relates to isolated polynucleotides having a nucleotide sequence which encode a polypeptide of the present invention. In a preferred aspect, the nucleotide sequence is set forth in SEQ ID NO: 1. In another more preferred aspect, the nucleotide sequence is the sequence contained in plasmid pBM115a that is contained in *Escherichia coli* NRRL B-30669. The present invention also encompasses nucleotide sequences which encode a polypeptide having the amino acid sequence of SEQ ID NO: 2, which differ from SEQ ID NO: 1 by virtue of the degeneracy of the genetic code. The present invention also relates to subsequences of SEQ ID NO: 1 which encode fragments of SEQ ID NO: 2 that have oxaloacetate hydrolase activity.

The present invention also relates to mutant polynucleotides comprising at least one mutation in the polypeptide coding sequence of SEQ ID NO: 1, in which the mutant nucleotide sequence encodes a polypeptide which consists of SEQ ID NO: 2.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, PCR: *A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Ceriporiopsis*, or another or related organism and thus, for example, may be an allelic or species variant of the polypeptide encoding region of the nucleotide sequence.

The present invention also relates to polynucleotides having nucleotide sequences which have a degree of identity to SEQ ID NO: 1 of at least 70%, preferably at least 75%, more preferably at least 80%, more preferably at least 85%, more preferably at least 90%, even more preferably at least 95%, and most preferably at least 97% identity, which encode an active polypeptide.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the polypeptide encoding region of SEQ ID NO: 1, e.g., a subsequence thereof, and/or by introduction of nucleotide substitutions which do not give rise to another amino acid sequence of the polypeptide encoded by the nucleotide sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95–107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081–1085). In the latter technique, mutations are introduced at every positively charged residue in the molecule, and the resultant mutant molecules are tested for oxaloacetate hydrolase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306–312; Smith et al., 1992, *Journal of Molecular Biology* 224: 899–904; Wlodaver et al., 1992, *FEBS Letters* 309: 59–64).

The present invention also relates to isolated polynucleotides encoding a polypeptide of the present invention, which hybridize under very low stringency conditions, preferably low stringency conditions, more preferably medium stringency conditions, more preferably medium-high stringency conditions, even more preferably high stringency conditions, and most preferably very high stringency conditions with (i) SEQ ID NO: 1, (ii) the cDNA sequence contained in SEQ ID NO: 1, or (iii) a complementary strand of (i) or (ii); or allelic variants and subsequences thereof (Sambrook et al., 1989, supra), as defined herein.

The present invention also relates to isolated polynucleotides obtained by (a) hybridizing a population of DNA under very low, low, medium, medium-high, high, or very high stringency conditions with (i) SEQ ID NO: 1, (ii) the cDNA sequence contained in SEQ ID NO: 1, or (iii) a complementary strand of (i) or (ii); and (b) isolating the hybridizing polynucleotide, which encodes a polypeptide having oxaloacetate hydrolase activity.

Nucleic Acid Constructs

The present invention also relates to nucleic acid constructs comprising an isolated polynucleotide of the present invention operably linked to one or more control sequences which direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence which is recognized by a host cell for expression of a polynucleotide encoding a polypeptide of the present invention. The promoter sequence contains transcriptional control sequences which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase, *Fusarium oxysporum* trypsin-like protease (WO 96/00787), *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionine (CUP1), and *Saccharomyces cerevisiae* 3-phosphoglycerate kinase. Other useful promoters for yeast host cells are described by Romanos et al., 1992, *Yeast* 8: 423–488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983–5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described herein may be joined together to produce a recombinant expression vector which may include one or more convenient restriction sites to allow for insertion or substitution of the nucleotide sequence encoding the polypeptide at such sites. Alternatively, a nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed, transfected, transduced, or the like cells. A selectable marker is a gene the product of which provides for biocide or viral resistance, resistance to heavy metals, prototrophy to auxotrophs, and the like.

Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98:61–67; Cullen et al., 1987, *Nucleic Acids Research* 15: 9163–9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into the host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred aspect, the yeast host cell is a *Candida, Hansenula, Kluyveromyces, Pichia, Saccharomyces, Schizosaccharomyces*, or *Yarrowia* cell.

In a most preferred aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In another most preferred aspect, the filamentous fungal host cell is a *Bjerkandera adusta, Ceriporiopsis subvermispora, Coprinus cinereus, Coriolus hirsutus, Humicola insolens, Humicola lanuginosa, Mucor miehei, Mycellophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* strain cell. In an even most preferred aspect, the filamentous fungal strain is a *Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa*, or *Ceriporiopsis subvermispora* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470–1474. Suitable methods for transforming *Fusarium* species are described by Malardier et al., 1989, *Gene* 78: 147–156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182–187, Academic Press, Inc., New York; Ito et al., 1983, *Journal of Bacteriology* 153: 163; and Hinnen et al., 1978, *Proceedings of the National Academy of Sciences USA* 75: 1920. *Ceriporiopsis* may be transformed using the methods for *Aspergillus* or *Fusarium* described above.

Methods of Production

The present invention also relates to methods for producing a polypeptide of the present invention, comprising (a) cultivating a cell, which in its wild-type form is capable of producing the polypeptide, under conditions conducive for production of the polypeptide; and (b) recovering the polypeptide. Preferably, the cell is of the genus *Ceriporiopsis*, and more preferably *Ceriporiopsis subvermispora*.

The present invention also relates to methods for producing a polypeptide of the present invention, comprising (a) cultivating a host cell under conditions conducive for production of the polypeptide; and (b) recovering the polypeptide.

The present invention also relates to methods for producing a polypeptide of the present invention, comprising (a) cultivating a host cell under conditions conducive for production of the polypeptide, wherein the host cell comprises a mutant nucleotide sequence having at least one mutation in the polypeptide coding region of SEQ ID NO: 1, wherein the mutant nucleotide sequence encodes a polypeptide which consists of SEQ ID NO: 2, and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

Plants

The present invention also relates to a transgenic plant, plant part, or plant cell which has been transformed with a nucleotide sequence encoding a polypeptide having oxaloacetate hydrolase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as Festuca, Lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide of the present invention may be constructed in accordance with methods known in the art. In short, the plant or plant cell is constructed by incorporating one or more expression constructs encoding a polypeptide of the present invention into the plant host genome and propagating the resulting modified plant or plant cell into a transgenic plant or plant cell.

The expression construct is conveniently a nucleic acid construct which comprises a polynucleotide encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed.

For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21: 285–294, Christensen et al., 1992, *Plant Mo. Biol.* 18: 675–689; Zhang et al., 1991, *Plant Cell* 3: 1155–1165). Organ-specific promoters may be, for example, a promoter from storage sink tissues such as seeds, potato tubers, and fruits (Edwards and Coruzzi, 1990, *Ann. Rev. Genet* 24: 275–303), or from metabolic sink tissues such as meristems (Ito et al., 1994, *Plant Mol. Biol.* 24: 863–878), a seed specific promoter such as the glutelin, prolamin, globulin, or albumin promoter from rice (Wu et al., 1998, *Plant and Cell Physiology* 39: 885–889), a *Vicia faba* promoter from the legumin B4 and the unknown seed protein gene from *Vicia faba* (Conrad et al., 1998, *Journal of Plant Physiology* 152: 708–711), a promoter from a seed oil body protein (Chen et al., 1998, *Plant and Cell Physiology* 39: 935–941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991–1000, the chlorella virus adenine methyltransferase gene promoter (Mitra and Higgins, 1994, *Plant Molecular Biology* 26: 85–93), or the aldP gene promoter from rice (Kagaya et al., 1995, *Molecular and General Genetics* 248: 668–674), or a wound inducible promoter such as the potato pin2 promoter (Xu et al., 1993, *Plant Molecular Biology* 22: 573–588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron which is placed between the promoter and the nucleotide sequence encoding a polypeptide of the present invention. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15–38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275–281; Shimamoto, 1994, *Current Opinion Biotechnology* 5: 158–162; Vasil et al., 1992, *Bio/Technology* 10: 667–674). An alternative method for transformation of monocots is based on protoplast transformation as described by Omirulleh et al., 1993, *Plant Molecular Biology* 21: 415–428.

Following transformation, the transformants having incorporated the expression construct are selected and regenerated into whole plants according to methods well-known in the art. Often the transformation procedure is designed for the selective elimination of selection genes either during regeneration or in the following generations by using, for example, co-transformation with two separate T-DNA constructs or site specific excision of the selection gene by a specific recombinase.

The present invention also relates to methods for producing a polypeptide of the present invention comprising (a) cultivating a transgenic plant or a plant cell comprising a polynucleotide encoding a polypeptide having oxaloacetate hydrolase activity of the present invention under conditions conducive for production of the polypeptide; and (b) recovering the polypeptide.

Removal or Reduction of Oxaloacetate Hydrolase Activity

The present invention also relates to methods for producing a mutant of a parent cell, which comprises disrupting or deleting a polynucleotide sequence, or a portion thereof, encoding a polypeptide of the present invention, which results in the mutant cell producing less of the polypeptide than the parent cell when cultivated under the same conditions.

The mutant cell may be constructed by reducing or eliminating expression of a nucleotide sequence encoding a polypeptide of the present invention using methods well known in the art, for example, insertions, disruptions, replacements, or deletions. In a preferred aspect, the nucleotide sequence is inactivated. The nucleotide sequence to be modified or inactivated may be, for example, the coding region or a part thereof essential for activity, or a regulatory element required for the expression of the coding region. An example of such a regulatory or control sequence may be a promoter sequence or a functional part thereof, i.e., a part that is sufficient for affecting expression of the nucleotide sequence. Other control sequences for possible modification include, but are not limited to, a leader, polyadenylation sequence, propeptide sequence, signal peptide sequence, transcription terminator, and transcriptional activator.

Modification or inactivation of the nucleotide sequence may be performed by subjecting the parent cell to mutagenesis and selecting for mutant cells in which expression of the nucleotide sequence has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the nucleotide sequence may be accomplished by introduction, substitution, or removal of one or more nucleotides in the gene or a regulatory element required for the transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleotide sequence to be modified, it is preferred that the modification be performed in vitro as exemplified below.

An example of a convenient way to eliminate or reduce expression of a nucleotide sequence by a cell is based on techniques of gene replacement, gene deletion, or gene disruption. For example, in the gene disruption method, a nucleic acid sequence corresponding to the endogenous nucleotide sequence is mutagenized in vitro to produce a defective nucleic acid sequence which is then transformed into the parent cell to produce a defective gene. By homologous recombination, the defective nucleic acid sequence replaces the endogenous nucleotide sequence. It may be desirable that the defective nucleotide sequence also encodes a marker that may be used for selection of transformants in which the nucleotide sequence has been modified or destroyed. In a particularly preferred aspect, the nucleotide sequence is disrupted with a selectable marker such as those described herein.

Alternatively, modification or inactivation of the nucleotide sequence may be performed by established anti-sense techniques using a sequence complementary to the nucleotide sequence. More specifically, expression of the nucleotide sequence by a cell may be reduced or eliminated by introducing a sequence complementary to the nucleotide sequence of the gene that may be transcribed in the cell and is capable of hybridizing to the mRNA produced in the cell. Under conditions allowing the complementary anti-sense nucleotide sequence to hybridize to the mRNA, the amount of protein translated is thus reduced or eliminated.

The present invention further relates to a mutant cell of a parent cell which comprises a disruption or deletion of a nucleotide sequence encoding the polypeptide or a control sequence thereof, which results in the mutant cell producing less of the polypeptide or no polypeptide compared to the parent cell.

The polypeptide-deficient mutant cells so created are particularly useful as host cells for the expression of native and/or heterologous polypeptides. Therefore, the present invention further relates to methods for producing a homologous or heterologous polypeptide comprising (a) cultivating the mutant cell under conditions conducive for production of the polypeptide; and (b) recovering the polypeptide. The term "heterologous polypeptides" is defined herein as polypeptides which are not native to the host cell, a native protein in which modifications have been made to alter the native sequence, or a native protein whose expression is quantitatively altered as a result of a manipulation of the host cell by recombinant DNA techniques.

In a further aspect, the present invention relates to a method for producing a protein product essentially free of oxaloacetate hydrolase activity by fermentation of a cell which produces both a polypeptide of the present invention as well as the protein product of interest by adding an effective amount of an agent capable of inhibiting oxaloacetate hydrolase activity to the fermentation broth before, during, or after the fermentation has been completed, recovering the product of interest from the fermentation broth, and optionally subjecting the recovered product to further purification.

In a further aspect, the present invention relates to a method for producing a protein product essentially free of oxaloacetate hydrolase activity by cultivating the cell under conditions permitting the expression of the product, subjecting the resultant culture broth to a combined pH and temperature treatment so as to reduce the oxaloacetate hydrolase activity substantially, and recovering the product from the culture broth. Alternatively, the combined pH and temperature treatment may be performed on an enzyme preparation recovered from the culture broth. The combined pH and temperature treatment may optionally be used in combination with a treatment with a oxaloacetate hydrolase inhibitor.

In accordance with this aspect of the invention, it is possible to remove at least 60%, preferably at least 75%, more preferably at least 85%, still more preferably at least 95%, and most preferably at least 99% of the oxaloacetate hydrolase activity. Complete removal of oxaloacetate hydrolase activity may be obtained by use of this method.

The combined pH and temperature treatment is preferably carried out at a pH in the range of 8–9 and a temperature in the range of 65–70° C. for a sufficient period of time to attain the desired effect, where typically, 30 to 60 minutes is sufficient.

The methods used for cultivation and purification of the product of interest may be performed by methods known in the art.

The methods of the present invention for producing an essentially oxaloacetate hydrolase-free product is of particular interest in the production of eukaryotic polypeptides, in particular fungal proteins such as enzymes. The enzyme may be selected from, e.g., an amylolytic enzyme, lipolytic enzyme, proteolytic enzyme, cellulytic enzyme, oxidoreductase, or plant cell-wall degrading enzyme. Examples of such enzymes include an aminopeptidase, amylase, amyloglucosidase, carbohydrase, carboxypeptidase, catalase, cellulase, chitinase, cutinase, cyclodextrin glycosyltransferase, deoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or xylanase. The oxaloacetate hydrolase-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from oxaloacetate hydrolase activity which is produced by a method of the present invention.

Compositions

The present invention also relates to compositions comprising a polypeptide of the present invention. Preferably, the compositions are enriched in such a polypeptide. The term "enriched" indicates that the oxaloacetate hydrolase activity of the composition has been increased, e.g., with an enrichment factor of 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, preferably *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, or *Aspergillus oryzae*; *Fusarium*, preferably *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sulphureum*, *Fusarium toruloseum*, *Fusarium trichothecioides*, or *Fusarium venenatum*; *Humicola*, preferably *Humicola insolens* or *Humicola lanuginosa*; or *Trichoderma*, preferably *Trichoderma harzianum*, *Trichoderma koningii*, *Trichoderma longibrachiatum*, *Trichoderma reesei*, or *Trichoderma viride*.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention is also directed to methods for using the polypeptides having oxaloacetate hydrolase activity.

The polypeptides of the present invention may be used as a diagnostic enzyme, e.g., for the detection of oxalic acid in food or other products.

The nucleotide sequences of the present invention may be used for modification of the production of oxaloacetate hydrolase and thus oxalic acid by a cell, such as a microbial cell normally producing the hydrolase. In particular, the nucleotide sequences may be used to reduce or eliminate oxaloacetate hydrolase and thus oxalic acid production of the cell in question.

Strains may be constructed, as described herein, to overproduce a polypeptide of the present invention to improve the lignin degradative ability of the strain. In a preferred aspect, the strain is a white rot fungus known to be involved in the degradation of lignin. In a more preferred aspect, the strain is *Ceriporiopsis* strain. In an even more preferred aspect, the strain is *Ceriporiopsis aneirina*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, or *Ceriporiopsis subvermispora* strain. In a most preferred aspect, the strain is *Ceriporiopsis subvermispora*, and most preferably *Ceriporiopsis subvermispora* FPL 104807SS-5. In another more preferred aspect, the strain is a *Bjerkandera*, *Coprinus*, *Coriolus*, *Humicola*, *Phanerochaete*, *Phlebia*, *Pleurotus*, *Thielavia*, *Trametes*, or *Trichoderma* strain. In another most preferred aspect, the strain is a *Bjerkandera adusta*, *Coprinus cinereus*, *Coriolus hirsutus*, *Humicola insolens*, *Humicola lanuginosa*, *Phanerochaete chrysosporium*, *Phlebia radiata*, *Pleurotus eryngii*, *Thielavia terrestris*, *Trametes villosa*, *Trametes versicolor*, *Trichoderma harzianum*, *Trichoderma koningii*, *Trichoderma longibrachiatum*, *Trichoderma reesei*, or *Trichoderma viride* strain.

The improved strains may then be used for the colonization of lignin-containing material, for example, wood, using the procedures described by Messner and Srebotnik, 1994, *FEMS Microb. Rev.* 13: 351–364; Scott and Swaney, 1998, *TAPPI J.* 81: 153–175; and Breen and Singleton, 1999, *Curr. Opinion Biotech.* 10: 252–258.

The present invention is further described by the following examples which should not be construed as limiting the scope of the invention.

EXAMPLES

Chemicals used as buffers and substrates were commercial products of at least reagent grade.

Media and Solution

PDA plates were composed per liter of 39 grams of potato dextrose agar.

YEG was composed per liter of 5 g of yeast extract and 20 g of glucose.

LB medium (pH 7.4) was composed per liter of 10 g of bacto-tryptone, 5 g of yeast extract, and 10 g of NaCl pH 7.4.

2×LB medium (pH 7.4) was composed per liter of 20 g of bacto-tryptone, 10 g of yeast extract, and 20 g of NaCl pH 7.4.

Basal minimal medium was composed per liter of 10 g of glucose, 1 mM ammonium tartrate, 10 mM transaconitic acid (pH 4.5), 2 g of $KH_2PO_4$, 0.5 g of $MgSO_4.7H_2O$, 0.1 g of $CaCl_2.2H_2O$, 1 mg of thiamine hydrochloride, and 1 ml of trace elements solution.

Trace elements solution was composed per liter of 15 g of nitroacetic acid, 1 g of $FeSO_4.7H_2O$, 1.8 g of $CoCl_2.6H_2O$, 1 g of $ZnCl_2.7H_2O$, 0.07 g of $Al_2(SO_4)_3.18H_2O$, 0.1 g of $CuSO_4.5H_2O$, 0.1 g of $H_3BO_3$, 0.1 g of $NaMoO_4.2H_2O$, 30 g of $MgSO_4.7H_2O$, 10 g of NaCl, 0.82 g of $CaCl_2$, and 0.5 g of $MnSO_4$.

2×YT plates were composed per liter of 15 g of Bacto Tryptone, 10 g of yeast extract, and 5 g of NaCl.

SOC medium was composed per liter of 20 g of Bacto Tryptone, 5 g of yeast extract, 2 ml of 5 M NaCl, and 2.5 ml of 1M KCl.

Example 1

Isolation of Genomic DNA from *Ceriporiopsis subvermispora*

A quarter inch square of agar of *Ceriporiopsis subvermispora* FPL 104807SS-5 (Forest Products Laboratory, Madison, Wis.) mycelia from a PDA plate was inoculated into 250 ml of YEG medium and incubated at 28° C. for 5 days. The mycelia were harvested by filtration through Miracloth (Calbiochem, San Diego, Calif.) and were frozen quickly in liquid nitrogen. Genomic DNA was isolated according to the procedure of Walheitner et al., 1996, *Current Genetics* 29: 395–403. The DNA pellet was resuspended in 500 µl of TE buffer (10 mM Tris-1 mM EDTA), and 5 µl was electrophoresed on a 1% agarose gel using TAE buffer (4.84 g of Tris Base, 1.14 ml of glacial acetic acid, and 2 ml of 0.5 M EDTA pH 8.0 per liter) to confirm the quality of the preparation.

Example 2

Construction of a *Ceriporiopsis subvermispora* Genomic Library

A total of 30 µg of *Ceriporiopsis subvermispora* genomic DNA was digested with Tsp509I (New England Biolabs, Beverly, Mass.) in a total volume of 150 µl using the manufacturer's recommended conditions. Aliquots of 30 µl of the digested DNA were removed at 10, 11, 12, 14, and 16 minutes after the addition of Tsp509I. The digestions were electrophoresed on a 0.8% agarose gel using TAE buffer. A gel slice containing 2 to 3 kb of digested DNA was removed, and the DNA fragments were purified using β-agarase (New England Biolabs, Beverly, Mass.) following the manufacturer's protocols.

A total of 3 µg of pUC19 was digested with EcoRI and treated with shrimp alkaline phosphatase (Amersham Pharmacia Biotech, Arlington Heights, Ill.) following the manufacturer's protocols. The digested DNA was electrophoresed on a 0.8% agarose gel using TAE buffer, and the gel slice containing the linearized plasmid was excised from the gel. The plasmid DNA was isolated from the gel slice using a Qiaquick spin column (QIAGEN, Chatsworth, Calif.).

The 2–3 kb Tsp509I genomic fragments and the EcoRI digested pUC19 were ligated together overnight at room temperature with T4 DNA ligase (New England Biolabs, Beverly, Mass.). The ligation reaction was precipitated by adding 1/10 volume of 3 M sodium acetate pH 5.0 and 2.5 volumes of 95% ethanol, incubating on ice for 30 minutes, and centrifuging at 12,000×g for 30 minutes. The ligated DNA was resuspended in 10 µl of TE buffer.

Three 40 µl aliquots of *E. coli* Electromax DH10B competent cells (Gibco BRL, Bethesda, Md.) were transformed with 1 µl of the ligated DNA by electroporation at a time constant of 2.3 at 2.5 kV, 25 µF, 100 Ω in a 0.1 cm cuvette. After transformation the cells were centrifuged at 1660×g for 5 to 10 minutes. The supernatant was carefully removed and the pelleted cells were resuspended in 0.5 ml of 2×LB medium plus 0.5 ml of 50% sterile glycerol. The transformants were frozen quickly in a dry ice ethanol bath and then frozen at −80° C.

The three transformations were titered after 1 day at −80° C. by plating on LB plates supplemented with 100 µg of ampicillin per ml. The total number of independent transformants obtained were approximately 23,000, 32,500, and 34,500 per transformation. The frozen glycerol stocks were sent to Genome Systems (St. Louis, Mo.) for colony picking. A library of approximately 50,000 in 384-well plates was obtained.

Example 3

Isolation of RNA from *Ceriporiopsis subvermispora*

Six 1 liter flasks with 29 ml of basal minimal medium were incubated with agar plugs from a PDA plate containing *Ceriporiopsis subvermispora* mycelia. The flasks were incubated at 28° C. without shaking for 15 days. The mycelia mats were harvested from the flasks and homogenized in sterile water in a Waring blender three times for 15 seconds with 30 second intervals to prevent the mycelia from warming. The homogenized mycelia were added to a 1 liter flask containing 20 gm of hardwood thermomechanical pulp that had previously been processed in a Waring blender for 30 seconds, and the mixture was stirred. For the minimal medium cultures, the homogenized mycelia were added to 15 ml of minimal medium in 1 liter flasks. The cultures were incubated at 30° C. for 30 days without shaking and the entire pulp culture containing pulp plus mycelia was frozen quickly in liquid nitrogen. The mycelia from the minimal medium culture were harvested by filtration through Miracloth and quickly frozen in liquid nitrogen.

RNA was prepared from the culture using a phenol/chloroform extraction as described below. Fresh p-aminosalicylic (PAS) (Sigma Chemical Co., St. Louis, Mo.) solution was prepared by mixing 9.6 gm in 80 ml of diethylpyrocarbonate (DEP)-treated water (Amresco, Solon, Ohio). Fresh tri-isopropylnaphthalene sulfonic acid (TNS) solution was prepared by mixing 1.6 gm in 80 ml of DEP-treated water. A 5×RNB solution was prepared by adding 24.2 g of Tris-HCl, 14.6 g of NaCl and 19 g of EGTA to 200 ml of DEP-treated water and adjusting the pH to 8.5 with NaOH. RNA extraction buffer was prepared by adding the PAS solution to the TNS solution while stirring. The PAS/TNS mixture was then added to 40 ml of RNB while stirring, and the final solution was placed on ice.

The frozen mycelia or mycelia plus pulp were ground to a fine powder in a coffee grinder that was prechilled with a few chips of dry ice. The powder was immediately added to 20 ml of RNA extraction buffer followed by 0.5 volumes of phenol/chloroform (1:1 v/v), and the mixture was placed on ice. A 0.25 volume of phenol/chloroform (1:1 v/v) was added and the phases were separated by centrifugation at 800×g for 10 minutes. The aqueous phase was removed and placed on ice in a fresh 50 ml tube containing a few drops of phenol/chloroform (1:1 v/v). The organic phase was mixed with 2 ml of extraction buffer, incubated in a water bath at 68° C. for 5 minutes, and centrifuged as above. The aqueous phase was combined with that saved on ice. The aqueous phase was then extracted four times with phenol/chloroform (1:1 v/v) until there was no protein at the interface. To precipitate the RNA, 0.1 volume of 3 M sodium acetate pH 5.2 plus 2.5 volumes of 95% ethanol was added and the mixture was frozen at −20° C. for 2 hours. The RNA was pelleted by centrifugation at 12,000×g for 20 minutes and resuspended in 450 µl of DEP-treated water. A 2 µl aliquot of each total RNA preparation was electrophoresed on a 0.8% agarose gel using TAE buffer to check the quality of the RNA.

Poly-A RNA was isolated using an mRNA Separator Kit (Clonetech, Palo Alto, Calif.) according to the manufacturer's protocols.

Example 4

Isolation of Plasmid DNA from the Genomic Library Clones

Each 384 well plate containing genomic clones was used to inoculate four 96-well deep well plates containing 1.25 ml of Magnificent Broth (MaCconnell Research, San Diego, Calif.) supplemented with ampicillin at 50 µg per ml. The 96-well deep well plates were incubated at 37° C. for 22–24 hours at 300 rpm. The plates were then centrifuged at 800×g for 10 minutes. Plasmid DNA was isolated using a Qiaprep Turbo Core Kit (QIAGEN, Chatsworth, Calif.) and a Qiagen BioRobot 9600 (QIAGEN, Chatsworth, Calif.) according to the manufacturer's instructions. The 96-well plates containing the plasmid DNA were dried down in a SpeedVac (Savant Instruments, Inc., Holbrook, N.Y.) followed by the addition of 15 µl of 3×SSC to each well using a Hydra HTS workstation (Robbins Scientific, Sunnyvale, Calif.).

Example 5

Printing of DNA Microarrays

Four 96-well plates were rearrayed back to 384-well plates using a Robbins Hydra HTS workstation. A 5 µl volume of each plasmid was aliquoted into 384-well microplates. From these plates, the plasmids were spotted onto poly-L-lysine coated glass microscope slides using the equipment and methods described in U.S. Pat. No. 5,807,522. The density of spots was 10,000 per slide.

Example 6

Probe Preparation and Hybridization

Fluorescent probes were prepared by reverse transcription of 1 µg of polyA RNA from *Ceriporiopsis subvermispora* to incorporate aminoallyl-dUTP into first strand cDNA. The amino-cDNA products were subsequently labeled by direct coupling to either Cy3 or Cy5 monofunctional reactive dyes (Amersham Pharmacia Biotech, Arlington Heights, Ill.). The details of this protocol are described by DeRisi et al., 1997, *Science* 278: 680–686. Cy3 and Cy5 labeled probes were combined and purified using Qiaquick PCR spin columns (QIAGEN, Valencia, Calif.). The purified probes were dried under vacuum in a SpeedVac, resuspended in 18 µl of water, and combined with the following: 3.6 µl of 20×SSC, 1.8 µl of poly-dA (500 µg/ml; Amersham Pharmacia Biotech), and 0.54 µl of 10% SDS. Before hybridization, the solution was filtered with a 0.22 µm Ultrafree-MC microcentrifuge filter (Millipore, Beford, Mass.), boiled for 2 minutes, and cooled to room temperature. The probe was then applied to the microarray under a coverglass, placed in a humidified chamber, and incubated at 65° C. overnight. Before scanning, the arrays were washed consecutively in 1×SSC with 0.03% SDS, 0.2×SSC, and 0.05×SSC, and centrifuged for 2 minutes at 500 rpm to remove excess liquid. Finally, the slides were imaged using a custom-built confocal laser microscope (Eisen and Brown, 1999, *Methods in Enzymology* 303: 179).

Example 7

Characterization of Clones Induced by Pulp

From the first 20,000 genomic clones (Example 2), 20 clones were determined to contain DNA whose expression was induced on hardwood thermomechanical pulp based on hybridization with the probe as described in Example 6. For each of the clones, plasmid DNA was isolated by inoculating 1 µl from the well of the 384 plate containing the desired clone into a 15 ml Falcon tube containing 3 ml of LB supplemented with 100 µg of ampicillin per ml. The clones were grown overnight at 37° C., 250 rpm.

Plasmids were then isolated using the QIAGEN robot protocol described in Example 5 and sequenced using 150 ng of plasmid template, 1.6 ng of M13 primer (forward or reverse), and water to 6 µl. The samples were run on an ABI 3700 Sequencer (Applied Biosystems, Foster City, Calif.). One of the clones, pCsubHP4 contained a genomic fragment, which shared identity to known oxaloacetate hydrolases but did not contain the whole gene.

Example 8

Utilizing RLM-RACE to Amplify the Complete Coding Sequence of a Oxaloacetate Hydrolase Total RNA was prepared according to the method outlined in Example 3. All of the steps in a RLM-RACE reaction were performed using a GeneRacer Kit (Invitrogen, Carlsbad, Calif.) according to the manufacturer's methodology. The RNA was subjected to a dephosphorylation reaction using 14 µl of total RNA (about 1 µg), 2 µl of CIP buffer (Invitrogen, Carlsbad, Calif.), 2 µl of RNaseOut (40 U/µl, Invitrogen, Carlsbad, Calif.), and 2 µl of calf intestinal phosphatase (10 U/µl). The reaction was mixed by pipette, vortexed briefly, and incubated at 50° C. for 1 hour. After the incubation the reactions were briefly centrifuged in a microcentrifuge and placed on ice.

The RNA was then precipitated using the following protocol. Volumes of 90 µl of DEPC water and 100 µl of phenol:chloroform 1:1 v/v were added to the samples and vortexed vigorously for 30 seconds. The samples were then centrifuged at maximum speed in a microcentrifuge for 5 minutes at room temperature. The aqueous (top) phase was transferred to a new microcentrifuge tube followed by 2 µl of mussel glycogen (10 mg/ml, Invitrogen, Carlsbad, Calif.), and 10 µl of 3 M sodium acetate pH 5.2, mixed well, and frozen on dry ice for 10 minutes. The RNA was subsequently pelleted by centrifugation at maximum speed in a microcentrifuge for 20 minutes at 4° C. The supernatant was removed by pipette being careful not to disturb the pellet. A 500 µl volume of 70% ethanol was then added to the pellet, inverted several times, vortexed briefly, and centrifuged at maximum velocity for 2 minutes at 4° C. in a microcentrifuge. The ethanol was removed by pipette and recentrifuged, and the step repeated to remove the final traces of ethanol remaining. The RNA pellet was air dried for 2 minutes at room temperature and then resuspended in 7 µl of DEPC water.

The mRNA cap structure was then removed with 7 µl of the dephosphorylated RNA, 1 µl of 10×tobacco acid pyrophosphatase buffer (Invitrogen, Carlsbad, Calif.), 1 µl of RNaseOut (40 U/µl), 1 µl of TAP (0.5 U/µl, Invitrogen, Carlsbad, Calif.), which was mixed by pipette and vortexed briefly. The fluid was collected by a short centrifuge pulse in a microcentrifuge and subsequently incubated at 37° C. for 1 hour. After incubation the samples were quickly centrifuged and placed on ice. The RNA was then precipitated as outlined above.

Once the mRNA cap structure was removed, ligation of a GeneRacer RNA oligo was performed by reacting 7 µl of dephosphorylated, decapped RNA with 0.25 µg of the GeneRacer RNA oligo shown below:

(SEQ ID NO: 3)
5'-CGACUGGAGCACGAGGACACUGACAUGGACUGAAGGAGUAGAAA-3'

The mixture was pipetted several times and then incubated at 65° C. for 5 minutes to remove the RNA secondary structure. After incubation the reaction was chilled on ice for 2 minutes followed by a brief centrifugation. To this mixture, 1 µl of 10×ligase buffer, 1 µl of 10 mM ATP, 1 µl of RNaseOut (40 U/µl), and 1 µl of T4 RNA ligase (5 U/µl) were added and incubated for 1 hour at 37° C. The reaction was then centrifuged briefly and placed on ice after which the RNA was precipitated up to the dry ice freezing step according to the precipitation protocol and afterward stored at −20° C. for the night.

The precipitation protocol was completed the next morning prior to the mRNA reverse transcription. The reverse transcription was carried out in 3 different reactions each with a different gene specific reverse primer. The primers were constructed to amplify 3'-ends of a partial gene fragment which appeared to be induced during growth of *Ceriporiopsis subvermispora* on pulp based on the procedure described in Example 3. The sequence was based upon the consensus sequence of the positive array clones. The different gene specific primers were as follows:

(1) 5'-GCCACCTGCTTGGCAAGCAGGTCGTCT-3' (Oligo ID# 993605 for the reverse transcription of the CsubHP4 gene encoding a oxaloacetate hydrolase) (SEQ ID NO: 4)

(2) 5'-ACCGGCTTCGGTGGTCCCGCTATGGTT-3' (Oligo ID# 993606 for the reverse transcription of the CsubHP4 gene encoding a oxaloacetate hydrolase. Located at a different position than (1)) (SEQ ID NO: 5)

(3) 5'-GAGCGCACAGATGGTCTGCAGCTTGM-3' (Oligo ID# 993607 for the reverse transcription of the CsubHP4 gene encoding a oxaloacetate hydrolase. Located at a different position than (1) and (2)) (SEQ ID NO: 6)

Volumes of 1 µl of the oligo dT primer (from the Gene Racer Kit) and 1 µl of dNTP mix (10 mM each) were added to 10 µl of the ligated RNA. The solution was incubated at 65° C. to remove any RNA secondary structure and then chilled on ice for 2 minutes. Next, 4 µl of 5×first strand buffer (Invitrogen, Carlsbad, Calif.), 2 µl of 0.1 M DTT, 1 µl of RNaseOut (40 U/µl), and 1 µl of Superscript II RT (200 U/µl, Invitrogen, Carlsbad, Calif.) were added to the primer and dNTP's, mixed, centrifuged briefly, and incubated at 42° C. for 50 minutes. After the incubation, the RT reaction was inactivated by heating to 70° C. for 15 minutes. The inactivated reaction was chilled on ice for 2 minutes and centrifuged briefly. A 1 µl volume of RNase H (2 units, Invitrogen, Carlsbad, Calif.) was added to the reaction mixture, incubated for 37° C. for 20 minutes, and then centrifuged briefly.

Once the total dT cDNA was synthesized, the sequence of interest was amplified by PCR amplification. Three amplification reactions (50 µl) were carried out using primers (1)-(3) above in combination with the GeneRacer dT oligo primer of SEQ ID NO: 3. The reaction mixture contained 3 µl of GeneRacer dT oligo primer (10 µM), 1 µl of reverse gene specific primer (10 µM), 2 µl RT template from the appropriate reaction, 5 µl of 10×Taq buffer (New England Biolabs, Beverly, Mass.), 1 µl of dNTP mix (10 mM each), 2.5 µl of DMSO, 34 µl of water, and 0.5 µl of Taq DNA polymerase (New England Biolabs, Beverly, Mass.). The reaction was incubated in a Eppendorf Mastercycler thermocycler (Eppendorf Scientific, Inc., Westbury, N.Y.), to run a touchdown PCR, programmed for 1 cycle at 94° C. for 2 minutes; 5 cycles each at 94° C. for 30 seconds and then 72° C. for 2 minutes; 5 cycles each at 94° C. for 30 seconds and then 70° C. for 2 minutes; 20 cycles each at 94° C. for 30 seconds, 65° C. for 30 seconds, and 68° C. for 2 minutes; 1 cycle at 68° C. for 10 minutes; and a 4° C. hold overnight.

A 10 µl volume of each PCR was mixed with 1.1 µl of loading buffer and run on a 0.8% agarose gel using TBE buffer (50 mM Tris base-50 mM boric acid-1 mM disodium EDTA) containing ethidium bromide at 90 V for 1 hour. The products were observed with UV light on a Nucleotech gel visualization system (Nucleotech, San Mateo, Calif.). The PCR amplifications providing products of approximately 900 bp were subjected to a round of nested PCR in order to increase concentration and purity. Nested PCR was carried out with the GeneRacer dT oligo primer and one of the gene specific primers as described above. The reactions were run under the same PCR conditions as described above except different templates and nested primers were used as described below:

(1) GeneRacer dT oligo and Primer (2) PCR product as template (2 µl) with the GeneRacer dT oligo primer and primer (1)

(2) GeneRacer dT oligo and Primer (3) PCR product as template (2 µl) with GeneRacer dT oligo primer and primer (1)

(3) GeneRacer dT oligo and Primer (3) PCR product as template (2 µl) with GeneRacer dT oligo primer and primer (2)

The PCR products were analyzed by agarose gel electrophoresis according to the first PCR reaction protocol described above. Products approximately 900 bp in size were ligated into a TOPO-TA vector (Invitrogen, Carlsbad, Calif.) according to the manufacturer's instructions by mixing 4 µl of the PCR product, 1 µl of salt solution (Invitrogen, Carlsbad, Calif.), and 1 µl of the TOPO-TA vector with a pipette and incubating at room temperature for 30 minutes.

After the incubation, OneShot competent *E. coli* cells (Invitrogen, Carlsbad, Calif.) were transformed with 2 µl of the ligation mixture and incubated on ice for 5 minutes. Subsequently the cells were heat shocked for 30 seconds at 42° C. and then placed on ice for 2 minutes. A 250 µl volume of SOC medium was added to the cells and the mixture was incubated for 1 hour at 37° C. and 250 rpm. After the incubation colonies were spread on 2×YT plates supplemented with 100 µg of ampicillin per ml and incubated at 37° C. overnight for selection of the plasmid. Colonies that grew on the plates were picked with a sterile toothpick, transferred to a 15 ml Falcon tube containing 3 ml of LB medium supplemented with 100 µg of ampicillin per ml, and incubated overnight at 37° C., 250 rpm.

Plasmids were isolated using the QIAGEN robot protocol described in Example 5. A 2 µl volume of the resulting plasmid minipreps were digested with EcoRI. The digestion reactions were analyzed by agarose electrophoresis as previously outlined for the PCR reactions to confirm the quality of the preparation.

Isolated plasmids containing an insert of approximately 900 bp were sequenced using 150 ng of plasmid template, 1.6 ng of M13 primer (forward or reverse), and 6 µl of water. The plasmid samples were sequenced using an ABI 3700 Sequencer (Applied Biosystems, Foster City, Calif.) and the sequences analyzed using Sequencher tools (Genecodes, Ann Arbor, Mich.) and blast alignments (NCBI, Bethesda, Md.) allowing for identification of an open reading frame for the oxaloacetate hydrolase gene.

Example 9

Utilizing RLM-RACE to Amplify the 5' End of the cDNA for the Oxaloacetate Hydrolase A RLM-RACE was performed to obtain the 5' cDNA sequence of the *Ceriporiopsis subvermispora* oxaloactetate hydrolase gene.

Total RNA from hardwood thermomechanical pulp treated for 30 days with *Ceriporiopsis subvermispora* was prepared according to the method outlined in Example 3. All of the steps in the RLM-RACE reaction were performed with materials provided in the GeneRacer Kit and carried out according to the manufacturer's methodology. The RNA was subjected to a dephosphorylation reaction using 5 µl of total RNA (about 1 µg), 2 µl CIP buffer, 2 µl RNaseOut (40 U/µl), and 2 µl CIP (10 U/µl). The reaction was mixed by pipette and vortexed briefly after which it was incubated at 50° C. for 1 hour. After incubation the reactions were briefly centrifuged and placed on ice.

The RNA was then precipitated and mRNA cap structure removed as described in Example 8. Once the mRNA cap structure was removed, ligation of the GeneRacer RNA oligo was performed as described in Example 8. The ligation mixture was stored at −20° C. overnight.

The frozen RNA ligation mixture was thawed and subsequently pelleted by centrifugation at maximum speed in a microcentrifuge for 20 minutes at 4° C. The supernatant was removed by pipetting being careful not to disturb the pellet. A 500 µl volume of 70% ethanol was then added to the pellet, inverted several times, vortexed briefly, and then centrifuged at maximum velocity for 2 minutes at 4° C. in a microcentrifuge. The ethanol was removed by pipette and the RNA pellet air dried for 2 minutes at room temperature and then resuspended in 7 µl of DEPC water.

Reverse transcription was performed using Random Primers (N$_6$) (Invitrogen, Inc., Carlsbad, Calif.). A 1 µl volume of random primer mix and 1 µl of dNTP mix (10 mM each) were added to the ligated RNA (10 µl). The mixture was incubated at 65° C. to remove any RNA secondary structure and then chilled on ice for 2 minutes. Then 4 µl of 5×first strand buffer (Invitrogen, Inc., Carlsbad, Calif.), 2 µl of 0.1 M DTT, 1 µl of RNaseOut (40 U/µl), and 1 µl of 15 U/µl Cloned AMV RT (Invitrogen, Inc., Carlsbad, Calif.) were added to the primer mix and dNTP's, mixed well, centrifuged briefly, and incubated at room temperature for 10 minutes to allow efficient binding of the Random Primer to the template. Immediately after the room temperature incubation the reaction mix was moved to a 42° C. water bath for 1 hour. After incubation, the reverse transcription reaction was inactivated by heating to 85° C. for 15 minutes, chilling on ice for 2 minutes, and centrifuging briefly.

Once the cDNA was synthesized, the fragment of interest was amplified by PCR using the Expand High Fidelity PCR system (Roche Diagnostics, Mannheim, Germany) with oligo 995222 in combination with the GeneRacer 5' primer shown below.

```
Oligo 995222:
5'-GGACTTCAGGAGCTCGGCGGT-3'       (SEQ ID NO: 7)

GeneRacer 5' primer:
5'-CGACTGGAGCACGAGGACACTGA-3'     (SEQ ID NO: 8)
```

The reaction mixture (50 µl) contained 1 µl of GeneRacer 5' primer (10 µM), 1 µl of reverse gene specific primer (50 pmol/µl), 5 µl of 10×PCR buffer with 15 mM MgCl$_2$, 1 µl of dNTP mix (10 mM each), 40.25 µl water, and 0.75 µl (3.5 U/µl) of DNA polymerase mix. The reaction was incubated in a Eppendorf Mastercycler thermocycler programmed for 1 cycle at 94° C. for 2 minutes; 10 cycles each at 94° C. for 15 seconds 50° C. for 30 seconds, 72° C. for 1.5 minutes; 15 cycles each at 94° C. for 15 seconds, 55° C. for 30 seconds, 72° C. for 1.5 minutes plus 5 second elongation at each successive cycle; 1 cycle at 72° C. for 7 minutes; and a 4° C. hold overnight.

Ten microliters of the PCR reaction was mixed with 1 µl of 10×DNA loading dye (25% glycerol, 10 mM Tris pH 7.0, 10 mM EDTA, 0.025% bromophenol blue, 0.025% xylene cyanol) and run on a 1.0% (w/v) agarose gel using TAE buffer. The products were observed with UV light on a Nucleotech gel visualization system. The PCR product was directly ligated into the pPCR4-TOPO vector (Invitrogen, Carlsbad, Calif.) according to the manufacturer's instructions. A 1 µl aliquot of fresh PCR product, 3 µl of double distilled water, and 1 µl of the TOPO cloning vector were mixed with a pipette and incubated at room temperature for 5 minutes.

After the incubation, OneShot competent *E. coli* cells were transformed with 2 µl of the ligation mixture and incubated on ice for 5 minutes. Subsequently the cells were heat shocked for 30 seconds at 42° C. and then placed on ice for 2 minutes. A 250 µl volume of SOC medium was added to the cells and the mixture was incubated for 1 hour at 37° C. and 250 rpm. After the incubation colonies were spread on 2×YT plates supplemented with 100 µg of ampicillin per ml and incubated at 37° C. overnight for selection of the plasmid.

Eight colonies that grew on the 2×YT plates were picked with a sterile toothpick, transferred to a 15 ml Falcon tube containing 3 ml of LB medium supplemented with 100 µg of ampicillin per ml, and incubated overnight at 37° C., 250 rpm. The plasmids were isolated using the QIAGEN robot protocol described in Example 5. A 4 µl volume of the resulting plasmid minipreps were digested with EcoRI. The digestion reactions were analyzed by agarose gel electrophoresis as previously described for the PCR reaction.

Isolated plasmids containing inserts were sequenced using 1 µl of plasmid template, 1.6 ng of M13 primer (forward or reverse), and 6 µl of water. DNA sequencing was performed with an Applied Biosystems Model 377 Sequencer XL using dye-terminator chemistry. From the sequence information, the 5' coding sequence of the *Ceriporiopsis subvermispora* oxaloactetate hydrolase gene was deduced.

Example 10

PCR Amplification of 3' Oxaloacetate Hydrolase Genomic Region

Primers were designed based on the 3' cDNA sequence for the oxaloacetate hydrolase gene from *Ceriporiopsis subver-*

*mispora*. The primers, shown below, were used to PCR amplify the 3' genomic region from *Ceriporiopsis subvernispora* genomic DNA.

```
Primer 995376:
                                        (SEQ ID NO: 9)
5'-GGTCGTCTCCCGCGAGGAATTCATGCACTCG-3'

Primer 995377:
                                       (SEQ ID NO: 10)
5'-CTAGACAACTTCGAACGCCTTGCCA-3'
```

The 3' fragment was amplified by PCR using the Expand High Fidelity PCR system (Roche Diagnostics, Mannheim, Germany). The PCR amplification reaction mixture contained 4 μl of *Ceriporiopsis subvermispora* genomic DNA, 1 μl of primer 995376 (50 pmol/μl), 1 μl of primer 995377 (50 pmol/μl), 5 μl of 10×PCR buffer (Roche Diagnostics, Mannheim, Germany) with 15 mM MgCl$_2$, 1 μl of dNTP mix (10 mM each), 37.25 μl of water, and 0.75 μl of DNA polymerase mix (3.5 U/μl, Roche Diagnostics, Mannheim, Germany). The reaction was incubated in a Eppendorf Mastercycler thermocycler programmed for 1 cycle at 94° C. for 2 minutes; 10 cycles each at 94° C. for 15 seconds, 55° C. for 30 seconds, and 72° C. for 1.5 minutes; 15 cycles each at 94° C. for 15 seconds, 55° C. for 30 seconds, and 72° C. for 1.5 minutes plus 5 second elongation at each successive cycle; 1 cycle at 72° C. for 7 minutes; and a 4° C. hold.

A re-amplification of the above described reaction was performed using 4 μl of the reaction mix, 1 μl of primer 995376 (50 pmol/μl), 1 μl of primer 995377 (50 pmol/μl), 5 μl of 10×PCR buffer with 15 mM MgCl$_2$, 1 μl of dNTP mix (10 mM each), 37.25 μl of water, and 0.75 μl of DNA polymerase mix (3.5 U/μl). The reaction was incubated in a Eppendorf Mastercycler thermocycler programmed for 1 cycle at 94° C. for 2 minutes; 10 cycles each at 94° C. for 15 seconds, 55° C. for 30 seconds, and 72° C. for 1.5 minutes; 15 cycles each at 94° C. for 15 seconds, 55° C. for 30 seconds, and 72° C. for 1.5 minutes plus 5 second elongation at each successive cycle; 1 cycle at 72° C. for 7 minutes; and 4° C. hold.

Ten microliters of the PCR reaction was mixed with 1 μl of 10×DNA loading dye and run on a 1.0% (w/v) agarose gel using TAE buffer. The products were observed with UV light on a Nucleotech gel visualization system. The PCR product (750 bp) was directly ligated into the pPCR2.1-TOPO vector (Invitrogen, Carlsbad, Calif.) according to the manufacturer's instructions. A 1 μl volume of fresh PCR product, 3 μl of water, and 1 μl of the TOPO cloning vector were mixed with a pipette and incubated on the bench top for 5 minutes.

After the incubation, 2 μl of the mixture was used to transform OneShot competent *E. coli* cells. A 2 μl volume of the ligation mixture was added to the *E. coli* and incubated on ice for 5 minutes. Subsequently, the cells were heat shocked for 30 seconds at 42° C., and then placed on ice for 2 minutes. A 250 μl volume of SOC medium was added to the cells and the mixture was incubated for 1 hour at 37° C. and 250 rpm. After the incubation the colonies were spread on 2×YT plates supplemented with 100 μg of ampicillin per ml and incubated at 37° C. overnight for selection of the plasmid.

Six colonies that grew on the plates were picked with a sterile toothpick and grown overnight at 37° C., 250 rpm in a 15 ml Falcon tube containing 3 ml of Luria Broth (LB) and 100 μg/ml of ampicillin. The plasmids were isolated using the QIAGEN robot protocol described in Example 5. A 4 μl volume of the resulting plasmid minipreps was digested with 0.5 μl of 10 U/μl EcoRI, 2 μl of 10×SURE/Cut buffer H (Roche Diagnostics, Mannheim, Germany, and 13.5 μl water for 2 hours at 37° C. The digestion reactions were analyzed by agarose gel electrophoresis as previously described for the PCR reaction. The resulting plasmid containing 3' genomic sequence of the *Ceriporiopsis subvermispora* oxaloactetate hydrolase gene was designated pBM113a.

Plasmid, pBM113a, was sequenced using 1 μl of plasmid template, 1.6 ng of M13 primer (forward or reverse), and water to 6 μl. DNA sequencing was performed with an Applied Biosystems Model 377 Sequencer XL using dye-terminator chemistry. DNA sequencing revealed two base pair substitutions in the oligomer sequence of pBM113a. Correction of the two base pair substitution within the pBM113a oligo sequence was accomplished using a QuikChange™ Site-Directed Mutagenesis Kit (Stratagene Cloning Systems, La Jolla, Calif.) according to the manufacturer's instructions with the following pairs of mutagenesis primers:

```
Primer 995424:
                                       (SEQ ID NO: 11)
5'-CTGATAGCCGGCGCAATCTTCTCTCTCGAGTCTTGCGTCGCG-3'

Primer 995425:
                                       (SEQ ID NO: 12)
5'-CGCGACGCAAGACTCGAGAGAGAAGATTGCGCCGGCTATCAG-3'
```

The PCR amplification reaction mixture contained 1 μl of pBM113a, 125 ng of primer 995424, 125 ng of primer 995425, 5 μl of 10×PCR buffer, 1 μl of dNTP mix (10 mM each), 40 μl of water, and 1 μl of pfu Turbo DNA polymerase (2.5 u/μl). The reaction was incubated in a Eppendorf Mastercycler thermocycler programmed for 1 cycle at 95° C. for 30 seconds; and 14 cycles each at 95° C. for 30 seconds, 68° C. for 9 minutes. After the completion of the PCR reaction, 1 μl of DpnI was added to the mixture and allowed to digest at 37° C. for 1 hour. Following digestion, the reaction mixture was added to transform Solopack Gold Supercompetent cells (Staratgene, La Jolla, Calif.). One μl of the mixture was added to cells thawed on ice. The cell/DNA mixture was incubated on ice for 30 minutes, followed by a 60 second heat pulse in a 54° C. water bath. A 250 μl volume of SOC medium was added to the cells and the mixture was incubated for 1 hour at 37° C. and 250 rpm. After the incubation colonies were spread on 2×YT plates supplemented with 100 μg of ampicillin per ml and incubated at 37° C. overnight for selection of the plasmid. Four colonies that grew on the plates were picked with a sterile toothpick and grown overnight at 37° C., 250 rpm in a 15 ml Falcon tube containing 3 ml of Luria Broth (LB) and 100 μg/ml of ampicillin. The plasmids were isolated using the QIAGEN robot protocol described in Example 5. A resulting plasmid, pBM114a, was sequenced using 1 μl of plasmid template, 1.6 ng of M13 primer (forward or reverse), and water to 6 μl. DNA sequencing was performed with an Applied Biosystems Model 377 Sequencer XL using dye-terminator chemistry. From the sequence information, the 3' genomic sequence of the *Ceriporiopsis subvermispora* oxaloactetate hydrolase gene was deduced.

Example 11

Construction of Full-length *Ceriporiopsis subvermispora* Oxaloactetate Hydrolase Genomic Clone Plasmid pBM115a (FIG. 2), containing the full-length oxaloacetate hydrolase genomic sequence was constructed. Plasmid, pBM114a, was digested with SmaI and BamHII, purified by agarose gel electrophoresis using standard methods (Sambrook et al., 1989, supra), and ligated to pCsubHP4 previously digested with BamHI and SmaI and then treated with shrimp alkaline phosphatase (Roche Diagnostics, Mannheim, Germany) following the manufacturer's protocols.

*E. coli* cells containing pBM115a were deposited with the Agricultural Research Service Patent Culture Collection, Northern Regional Research Center, 1815 University Street, Peoria, Ill., 61604, as NRRL B-30669, with a deposit date of Jun. 11, 2003.

The nucleotide sequence (SEQ ID NO: 1) and deduced amino acid sequence (SEQ ID NO: 2) of the *Ceriporiopsis subvermispora* oxaloacetate hydrolase are shown in FIG. 1. The insert contains an open reading frame of 1418 kb encoding a polypeptide of 363 amino acids. The open reading frame is interrupted by 6 introns of 58, 53, 55, 51, 49, and 60 bp. The % G+C content is 58.3%. The oxaloacetate hydrolase has a predicted molecular weight of 38261 kDa.

A comparative alignment of oxaloacetate hydrolase sequences was determined using the Clustal W method (Higgins, 1989, *CABIOS* 5: 151–153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5. The alignment showed that the deduced amino acid sequence of the *Ceriporiopsis subvermispora* oxaloacetate hydrolase gene shared 40.8% identity to the deduced amino acid sequence of an *Aspergillus niger* oxaloacetate hydrolase (GenSeq aay95923).

Deposit of Biological Material

The following biological material has been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
| --- | --- | --- |
| *E. coli* pBM115a | NRRL B-30669 | Jun. 11, 2003 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

---

What is claimed is:

1. An isolated polynucleotide encoding a polypeptide having oxaloacetate hydrolase activity, selected from the group consisting of:
 (a) a polynucleotide encoding a polypeptide having an amino acid sequence which has at least 95% identity with SEQ ID NO: 2;
 (b) a polynucleotide having at least 95% homology with SEQ ID NO: 1;
 (c) a polynucleotide which hybridizes under high stringency conditions with (i) SEQ ID NO: 1, (ii) the cDNA sequence encoding the polypeptide of SEQ ID NO: 2, or (iii) a complementary strand of (i) or (ii); and
 (d) a subsequence of (a), (b), or (c), wherein the subsequence encodes a polypeptide fragment which has oxaloacetate hydrolase activity.

2. The polynucleotide of claim 1, which encodes a polypeptide having an amino acid sequence which has at least 95% identity with SEQ ID NO: 2.

3. The polynucleotide of claim 1, which encodes a polypeptide comprising the amino acid sequence of SEQ ID NO: 2.

4. The polynucleotide of claim 1, which encodes a polypeptide consisting of the amino acid sequence of SEQ ID NO: 2, or a fragment thereof which has oxaloacetate hydrolase activity.

5. The polynucleotide of claim 4, which encodes a polypeptide consisting of the amino acid sequence of SEQ ID NO: 2.

6. The polynucleotide of claim 1, which has at least 95% homology with SEQ ID NO: 1.

7. The polynucleotide of claim 1, which has the nucleic acid sequence of SEQ ID NO: 1.

8. The polynucleotide of claim 1, wherein the nucleic acid sequence hybridizes under high stringency conditions with (i) SEQ ID NO: 1, (ii) the cDNA sequence that encodes the polypeptide of SEQ ID NO: 2, or (iii) a complementary strand of (i) or (ii).

9. The polynucleotide of claim 1, which is contained in the plasmid pBM115a which is contained in *E. coli* NRRL B-30669.

10. A nucleic acid construct comprising the polynucleotide of claim 1 operably linked to one or more control sequences which direct the production of the polypeptide in a suitable expression host.

11. A recombinant expression vector comprising the nucleic acid construct of claim 10, a promoter, and transcriptional and translational stop signals.

12. A recombinant host cell comprising the nucleic acid construct of claim 10.

13. A method for producing a polypeptide having oxaloacetate hydrolase activity comprising (a) cultivating the host cell of claim 12 under conditions suitable for production of the polypeptide; and (b) recovering the polypeptide.

14. The isolated polynucleotide, obtained by (a) hybridizing a population of DNA under high stringency conditions with (i) SEQ ID NO: 1, (ii) the cDNA sequence that encodes the polypeptide of SEQ ID NO: 2, or (iii) a complementary strand of (i) or (ii); and (b) isolating the hybridizing polynucleotide, which encodes a polypeptide having oxaloacetate hydrolase activity.

15. A method for producing the polypeptide having oxaloacetate hydrolase activity, comprising (a) cultivating a transgenic plant or a plant cell comprising the polynucleotide of claim 1 under conditions conducive for production of the polypeptide; and (b) recovering the polypeptide.

16. A transgenic plant, plant part or plant cell, which has been transformed with the polynucleotide of claim 1.

* * * * *

SEQUENCE LISTING

<160> NUMBER OF SEQ ID NOS: 12

<210> SEQ ID NO 1
<211> LENGTH: 1418
<212> TYPE: DNA
<213> ORGANISM: Ceriporiopsis subvermispora

<400> SEQUENCE: 1

```
atgccgggcc ttgactactt ccgcgagact gagaccactc aggtccctgc cccagttgcg      60
acgcaagagc ccgtagagtc tgagccttct tcccctgccg acaccatgcc catcgacaac     120
ggtcttaccc ctgctcctgg tgtctactac aaccccgcc tcgaccccaa aaactacctc     180
gaaggtcctc tctcgtggaa cccctcgacc cgtctccggc aactgctggc gcgtcctggt     240
atcgttgtaa gttccttcgt acactagaga tgaattgcac gctgattaaa ttttcgattt     300
gcaggtggcg cctggtatct gcgatggcat cagcgcacgc tgtgccttgg aggcgggctt     360
cgactgcatg taccagaggt acgtccagga tcgaattgta tgaatttcga agctgatttg     420
aacgtcttca gcggcgccgc caccaccgca tcccgtctcg gcatgcctga cctcgcaatc     480
```

-continued

```
gcaactctca acgacttcgt tcagagcgca cagatggtct gcagcttgaa cccctcggta      540
cccgtcattg ccgacgcaga caccggcttc ggtggtcccg ctatggttgc tcgtacggtc      600
acgcaatacg cgcgcgcagg tgtcgccgga ctccacatcg aggaccaggt tcagaccaag      660
cgctgcggcc acctgcttgg caagcaggtc gtctcccgcg aggaattcat cactcgcatt      720
cgggcagccg tcatcgcacg cgactccatc ccgggaggct cggacttcgt aagtccacat      780
ccaaattcaa ttgtcgacga atttgaatta acagcactcg taggtcatca ttggccgcac      840
ggactctgcc caggtcttgg gcatggagga ggcgatcatc cgcctgaagc tcgccgccga      900
tgccggagcg gatgtgtgct tcatcgaagg tgtgcgtacc gccgagctcc tgaagtccac      960
ggtggctgcg ctggcgccca gcctgtgagt tctcctcac cagatcggta tcgaagctgc      1020
ctaacatttc tatcaggtcc tcgtcaatgt catctcgggt ggtctgaccc cctccttcac      1080
ctgccaagag gccgaggaga tgggtgccaa gattatcagt aagtcttctc aaagtgagcc      1140
acctctgtgt actgatagcc ggcgcaatct tctctctcga gtcttgcgtc gcggccgtgc      1200
acggtatccg cgcggcgatg cactccctga agaagaccgg tacagacttc tcgtctgcga      1260
agggcatgga ccccaaggcg ttcttcgagg tcatgggtat gtcgtgccac caatgccaat      1320
ttcctcacag gcctgatggg tgatcatttg caacaggtct ccacgatgtc atcgagctcg      1380
acgcccaggc tggtggcaag gcgttcgaag ttgtctag                              1418
```

<210> SEQ ID NO 2
<211> LENGTH: 348
<212> TYPE: PRT
<213> ORGANISM: Ceriporiopsis subvermispora

<400> SEQUENCE: 2

```
Met Pro Gly Leu Asp Tyr Phe Arg Glu Thr Glu Thr Thr Gln Val Pro
1               5                   10                  15

Ala Pro Val Ala Thr Gln Glu Pro Val Glu Ser Glu Pro Ser Ser Pro
            20                  25                  30

Ala Asp Thr Met Pro Ile Asp Asn Gly Leu Thr Pro Ala Pro Gly Val
        35                  40                  45

Tyr Tyr Asn Pro Arg Leu Asp Pro Lys Asn Tyr Leu Glu Gly Pro Leu
    50                  55                  60

Ser Trp Asn Pro Ser Thr Arg Leu Arg Gln Leu Leu Ala Arg Pro Gly
65                  70                  75                  80

Ile Val Val Ala Pro Gly Ile Cys Asp Gly Ile Ser Ala Arg Cys Ala
                85                  90                  95

Leu Glu Ala Gly Phe Asp Cys Met Tyr Gln Ser Gly Ala Ala Thr Thr
            100                 105                 110

Ala Ser Arg Leu Gly Met Pro Asp Leu Ala Ile Ala Thr Leu Asn Asp
        115                 120                 125

Phe Val Gln Ser Ala Gln Met Val Cys Ser Leu Asn Pro Ser Val Pro
    130                 135                 140

Val Ile Ala Asp Ala Asp Thr Gly Phe Gly Gly Pro Ala Met Val Ala
145                 150                 155                 160

Arg Thr Val Thr Gln Tyr Ala Arg Ala Gly Val Ala Gly Leu His Ile
                165                 170                 175

Glu Asp Gln Val Gln Thr Lys Arg Cys Gly His Leu Leu Gly Lys Gln
            180                 185                 190

Val Val Ser Arg Glu Glu Phe Ile Thr Arg Ile Arg Ala Ala Val Ile
        195                 200                 205
```

```
Ala Arg Asp Ser Ile Pro Gly Gly Ser Asp Phe Val Ile Ile Gly Arg
    210                 215                 220

Thr Asp Ser Ala Gln Val Leu Gly Met Glu Glu Ala Ile Ile Arg Leu
225                 230                 235                 240

Lys Leu Ala Ala Asp Ala Gly Ala Asp Val Cys Phe Ile Glu Gly Val
                245                 250                 255

Arg Thr Ala Glu Leu Leu Lys Ser Thr Val Ala Ala Leu Ala Pro Lys
                260                 265                 270

Pro Cys Gln Glu Ala Glu Met Gly Ala Lys Ile Ile Ile Phe Ser
                275                 280                 285

Leu Glu Ser Cys Val Ala Ala Val His Gly Ile Arg Ala Ala Met His
    290                 295                 300

Ser Leu Lys Lys Thr Gly Thr Asp Phe Ser Ser Ala Lys Gly Met Asp
305                 310                 315                 320

Pro Lys Ala Phe Phe Glu Val Met Gly Leu His Asp Val Ile Glu Leu
                325                 330                 335

Asp Ala Gln Ala Gly Gly Lys Ala Phe Glu Val Val
                340                 345

<210> SEQ ID NO 3
<211> LENGTH: 44
<212> TYPE: DNA
<213> ORGANISM: Ceriporiopsis subvermispora
<220> FEATURE:
<221> NAME/KEY: misc_feature
<222> LOCATION: (5)..(5)
<223> OTHER INFORMATION: n= Uridine
<220> FEATURE:
<221> NAME/KEY: misc_feature
<222> LOCATION: (21)..(21)
<223> OTHER INFORMATION: n= Uridine
<220> FEATURE:
<221> NAME/KEY: misc_feature
<222> LOCATION: (26)..(26)
<223> OTHER INFORMATION: n= Uridine
<220> FEATURE:
<221> NAME/KEY: misc_feature
<222> LOCATION: (31)..(31)
<223> OTHER INFORMATION: n= Uridine
<220> FEATURE:
<221> NAME/KEY: misc_feature
<222> LOCATION: (39)..(39)
<223> OTHER INFORMATION: n= Uridine

<400> SEQUENCE: 3
cgacnggagc acgaggacac ngacanggac ngaaggagna gaaa                    44

<210> SEQ ID NO 4
<211> LENGTH: 27
<212> TYPE: DNA
<213> ORGANISM: Ceriporiopsis subvermispora

<400> SEQUENCE: 4
gccacctgct tggcaagcag gtcgtct                                        27

<210> SEQ ID NO 5
<211> LENGTH: 27
<212> TYPE: DNA
<213> ORGANISM: Ceriporiopsis subvermispora

<400> SEQUENCE: 5
accggcttcg gtggtcccgc tatggtt                                        27
```

```
<210> SEQ ID NO 6
<211> LENGTH: 27
<212> TYPE: DNA
<213> ORGANISM: Ceriporiopsis subvermispora

<400> SEQUENCE: 6
gagcgcacag atggtctgca gcttgaa                                           27

<210> SEQ ID NO 7
<211> LENGTH: 21
<212> TYPE: DNA
<213> ORGANISM: Ceriporiopsis subvermispora

<400> SEQUENCE: 7
ggacttcagg agctcggcgg t                                                 21

<210> SEQ ID NO 8
<211> LENGTH: 23
<212> TYPE: DNA
<213> ORGANISM: Ceriporiopsis subvermispora

<400> SEQUENCE: 8
cgactggagc acgaggacac tga                                               23

<210> SEQ ID NO 9
<211> LENGTH: 31
<212> TYPE: DNA
<213> ORGANISM: Ceriporiopsis subvermispora

<400> SEQUENCE: 9
ggtcgtctcc cgcgaggaat tcatgcactc g                                      31

<210> SEQ ID NO 10
<211> LENGTH: 25
<212> TYPE: DNA
<213> ORGANISM: Ceriporiopsis subvermispora

<400> SEQUENCE: 10
ctagacaact tcgaacgcct tgcca                                             25

<210> SEQ ID NO 11
<211> LENGTH: 42
<212> TYPE: DNA
<213> ORGANISM: Ceriporiopsis subvermispora

<400> SEQUENCE: 11
ctgatagccg gcgcaatctt ctctctcgag tcttgcgtcg cg                          42

<210> SEQ ID NO 12
<211> LENGTH: 42
<212> TYPE: DNA
<213> ORGANISM: Ceriporiopsis subvermispora

<400> SEQUENCE: 12
cgcgacgcaa gactcgagag agaagattgc gccggctatc ag                          42
```